United States Patent [19]

Sletzinger et al.

[11] Patent Number: 4,584,389

[45] Date of Patent: Apr. 22, 1986

[54] PROCESSES FOR PREPARING 6(R)-[2-[8(S)(2,2-DIMETHYLBUTYRYLOXY)-2(S),6(S)-DIMETHYL-1,2,3,4,4A(S),5,6,7,8-,8A(S)-DECAHYDRONAPHTHYL-1(S)]ETHYL]-4(R)-HYDROXY-3,4,5,6-TETRAHYDRO-2H-PYRAN-2-ONE

[75] Inventors: Meyer Sletzinger, North Plainfield; Thomas R. Verhoeven, Cranford; Ralph P. Volante, East Windsor, all of N.J.

[73] Assignee: Merck & Co., Inc., Rahway, N.J.

[21] Appl. No.: 737,361

[22] Filed: May 23, 1985

Related U.S. Application Data

[63] Continuation of Ser. No. 540,958, Oct. 11, 1983, abandoned.

[51] Int. Cl.[4] .................................... C07D 309/10
[52] U.S. Cl. .................................... 549/292; 560/256
[58] Field of Search ..................... 549/292; 560/256

[56] References Cited

U.S. PATENT DOCUMENTS

| | | | |
|---|---|---|---|
| 3,983,140 | 9/1976 | Endo et al. | 549/292 |
| 4,231,938 | 11/1980 | Monaghan et al. | 549/292 |
| 4,351,844 | 9/1982 | Patchett et al. | 549/292 |
| 4,490,546 | 12/1984 | Kuo | 549/292 |

FOREIGN PATENT DOCUMENTS 149247 9/1982 Japan.
885044 12/1961 United Kingdom.

OTHER PUBLICATIONS

Herbert O. House, Modern Synthetic Reactions, 2nd ed. (1972), pp. 1–3.
Kuo et al., JACS 93:23, (1971), pp. 6321–6323.
Dubois et al., Bull. Soc. Chim. Fr., (1963), pp. 1491–1496.
Ewing et al., J. Org. Chem. 40, (1975), pp. 2965–2966.
W. Carruthers, Some Modern Methods of Organic Synthesis, 2nd ed., p. 2.
R. G. Pearson et al., JACS 75, (1953), pp. 2439–2443.
Rathke et al., JACS 93:9, (1971), pp. 2318–2320.
John C. Stowell, Carbanions in Organic Synthesis, (1979), pp. 157–158.
Pfeffer et al., U. Org. Chem., vol. 37:3, (1972), pp. 451–458.
J. Herrmann et al., Tetrahedron Letters, No. 26, (1973), pp. 2429–2432.
Heathcock et al., J. Org. Chem., 45, (6), (1980), pp. 1066–1081.
Cregge et al., Tetrahedron Letters, No. 26, (1973), pp. 2425–2428.
M. Larcheveque et al., CA 84:179576b.
Warner et al., J. Org. Chem. (1982), vol. 47, pp. 893–895.
G. Frater, Tetrahedron Letters (1981), 22(5), pp. 425–428.
D. Seebach et al., Helv. Chim. Acta, 63(1), (1980), pp. 197–200.
P. L. Creger, JACS 89:10, (1967), pp. 2500–2501.

*Primary Examiner*—Norma S. Milestone
*Attorney, Agent, or Firm*—William H. Nicholson; Joseph F. DiPrima

[57] ABSTRACT

The compound 6(R)-[2-8(S)(2,2-dimethylbutyryloxy)-2(S),6(S)-dimethyl-1,2,3,4,4a(S),5,6,7,8,8a(S)-decahydronaphthyl-1(S)ethyl]-4(R)-hydroxy-3,4,5,6-tetrahydro-2H-pyran-2-one is prepared in two steps from mevinolin and comprise reduction of the two double bonds and C-methylation of the 8(S)-(2-methylbutyryloxy) group to form the 2,2-dimethylbutyryloxy group. The two steps can be performed in either order.

6 Claims, No Drawings

PROCESSES FOR PREPARING 6(R)-[2-[8(S)(2,2-DIMETHYLBUTYRYLOXY)-2(S),6(S)-DIMETHYL-1,2,3,4,4A(S),5,6,7,8,8A(S)-DECAHYDRONAPHTHYL-1(S)]ETHYL]-4(R)-HYDROXY-3,4,5,6-TETRAHYDRO-2H-PYRAN-2-ONE

This is a continuation of application Ser. No. 540,958, filed Oct. 11, 1983, now abandoned.

SUMMARY OF THE INVENTION

This invention is concerned with novel processes for the preparation of the compound of structural formula:

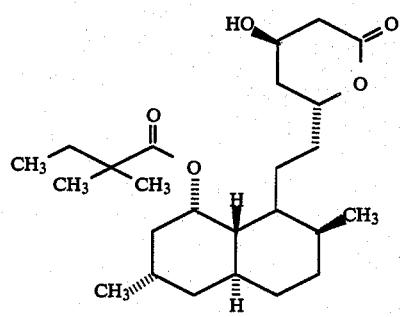

which comprises the steps in either order of (1) reduction of the two double bonds of mevinolin; and (2) methylation of the 2-methylbutyryloxy group of mevinolin to form the 2,2-dimethylbutyryloxy group.

Compound I is an antihypercholesterolemic agent useful in the treatment of atherosclerosis, hyperlipemia, familial hypercholesterolemia and like disorders.

BACKGROUND OF THE INVENTION

Mevinolin, the starting material for the novel process of this invention is a fermentation product described in U.S. Pat. No. 4,231,938.

Hydrogenation products, including tetrahydromevinolin are described in U.S. Pat. No. 4,351,844.

Compound I and processes for its preparation are disclosed in published European application EP No. 0033538. However, the processes disclosed involve five distinct chemical steps from mevinolin involving (1) reduction; (2) de-esterification of the 8-ester group; (3) protection of the 4-hydroxy of the pyranone group; (4) re-esterification with the desired 2,2-dimethylbutyryl; and (5) deprotection of the 4-hydroxy, not necessarily in that order.

Now, with the present invention there are provided novel processes for the preparation of Compound I involving only two chemical steps resulting in overall yields much higher than those realized by the prior art, with the expenditure of much less time, labor and materials.

DETAILED DESCRIPTION OF THE INVENTION

The novel processes of this invention are as depicted below:

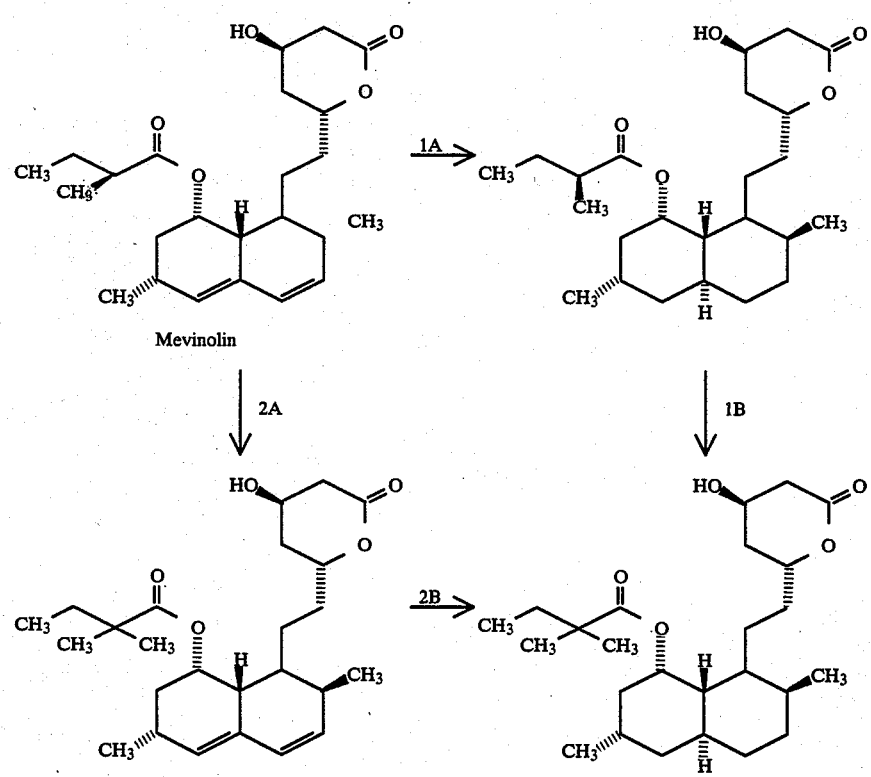

The reduction of the diene system of mevinolin described in the prior art, U.S. Pat. No. 4,351,844 utilized a PtO$_2$ catalyst, in ethyl acetate at room temperature and atmospheric pressure for about one hour.

However, using those conditions, at best a 60:40 mixture of trans:cis tetrahydromevinolin was produced. Furthermore, the desired trans compound could be isolated from this mixture only after extensive silica-gel column chromatographic purification. Attempts to improve this ratio were investigated using a variety of catalysts and solvents and lead to the novel process of the present invention.

The reduction depicted as process steps 1A and 2B comprises treatment of the starting material in an organic solvent with hydrogen in the presence of a platinum on alumina ($Pt/Al_2O_3$) catalyst with agitation.

The preferred catalyst is 5% $Pt/Al_2O_3$ but other catalysts such as 2 to 10% $Pt/Al_2O_3$ are useful.

The preferred solvent is ethyl acetate, but other solvents which can be employed include isopropyl acetate, hexanes, and methylene chloride or mixtures thereof.

The ratio of starting material to catalyst, by weight is about 3/1 to 6/1 and preferably about 4/1 to 5/1.

The concentration of starting material is about 1 g/30 ml to about 1 g/70 ml and preferably about 1 g/50 ml of solvent.

The reaction proceeds at hydrogen pressures at or above atmospheric pressure, preferably at about 30 to 50 psi and most preferably at about 40 psi for about 4 to 8 hours at about 15° to 40° C., preferably about 20°-25° C.

Employing conditions such as described, the reduction product is about 65 to 75% the desired trans isomer which can be isolated and separated from any by-products by direct crystallizaton in about 60% overall yield with a purity greater than 95%.

The process step depicted as 2A or 1B comprises C-methylation at the 2-position of the 2-methylbutyryloxy group at the 8-position of the polyhydronaphthalene moiety of mevinolin or its tetrahydro analog. The lactone compound is first converted to an alkali metal salt, preferably the potassium salt, of the dihydroxycarboxylate. Although any conceivable process for preparing a dry salt would suffice, it is convenient to add a stoichiometric amount of aqueous potassium hydroxide to a solution of the lactone starting material in a hydrocarbon solvent such as benzene, toluene, or cyclohexane containing a small amount of a $C_{1-3}$ alkanol, preferably isopropanol, ethanol or methanol, stirring for a few minutes to about an hour and finally concentrating to dryness in vacuo. The residue is subjected to rigorous drying such as by azeotropic distillation with cyclohexane or toluene, as the actual methylation procedure that follows proceeds properly only under rigorously anhydrous conditions.

The dry alkali metal salt is dissolved in an ethereal solvent such as tetrahydrofuran, diethyl ether, 1,2-dimethoxyethane, or the like, cooled to about −60° to about −25° C., preferably −35° to −30° C., and treated with an excess of a strong base such as an alkali metal amide, wherein the alkali metal is lithium, sodium or potassium, preferably lithium, and the amides are diethylamide, pyrrolidide, dimethyl amide or diisopropyl amide in an ethereal solvent in a dry inert environment. After about 2 to 8 hours, preferably about 2 hours at about −50° to −25° C., preferably −35° to −30° C., a methylhalide, such as methylbromide, methylchloride or methyl iodide, preferably methyl bromide, or methyl iodide, is added to the mixture while maintaining the low temperature. Treatment with a strong base and methyl halide as described can be repeated if appreciable quantities of starting material remain. After about 0.5 to about 3 hours, following final addition of methyl halide the reaction mixture is quenched by adding it to an excess of water. To isolate the product the aqueous phase is adjusted to pH 3-6 with a strong mineral acid such as hydrochloric, hydrobromic, sulfuric, phosphoric acid or the like. The aqueous phase is extracted with cyclohexane or toluene, dried, filtered, refluxed for 3-20 hours and finally concentrated, and filtered.

Recrystallization provides material of greater than 90% purity in about 60-70% yield over the C-methylation step.

EXAMPLE 1

6(R)-[2-[8(S)(2,2-dimethylbutyryloxy)-2(S),6(S)-dimethyl-1,2,3,4,4a(S),5,6,7,8,8a(S)-decahydronaphthyl-1(S)]ethyl]-4(R)-hydroxy-3,4,5,6,-tetrahydro-2H-pyran-2-one

Step A: Preparation of trans-tetrahydromevinolin

750 Mg of 5% $Pt/Al_2O_3$ catalyst was suspended in 75 ml of ethyl acetate in a 300 ml autoclave and stirred at 22°-25° and 1500 rpm under 40 psi of hydrogen pressure for one hour.

A solution of 3 g of mevinolin in 150 ml of ethyl acetate was then added at a rate of 0.5 ml/min. and the reaction temperature was maintained at 20°-25°. The final reaction mixture was then stirred under 40 psi of hydrogen pressure for an additional 16 hours. The reaction mixture was then filtered through a 2-3 inch plug of filter aid in a 15 ml coarse sintered glass funnel. The filter cake was washed with about 25 ml of ethyl acetate and the combined filtrates were concentrated to about 6 ml. Hexane (54 ml) was added and the mixture was heated to reflux (65°-68°). The solution was then cooled to 10° over 2 hours and aged at 10° for 2 hours. The solids were collected by filtration to yield 2.0 g of trans-tetrahydromevinolin (66% yield) of 99+% relative purity.

Step B: Preparation of 6(R)-[2-[8(S)(2,2-dimethylbutyryloxy-2(S),6(S)-dimethyl-1,2,3,4,4a(S),5,6,7,8,8a(S)-decahydronaphthyl-1(S)]ethyl]-4(R)-hydroxy-3,4,5,6-tetrahydro-2H-pryan-2-one A solution of trans-tetrahydro mevinolin (5 g, 12.25 mmol) in cyclohexane (100 ml) and isopropanol (12 ml) was prepared under nitrogen. An aqueous solution of potassium hydroxide (4.91M, 2.5 ml, 12.27 mmol) was added in one portion and the two-phase mixture stirred for 0.5 hr. at ambient temperature. The mixture was concentrated via distillation (bath temperature 100° C.). The vessel was recharged with 150 ml of cyclohexane and reconcentrated to a volume of 15 ml. The potassium carboxylate solution was diluted with tetrahydrofuran (35 ml) and cooled to −35° C.

A solution of pyrrolidine (3.6 ml, 43.1 mmol) in tetrahydrofuran (30 ml) was cooled to −5° C. and a solution of n-butyllithium (27.5 ml, 42.6 mmol, 1.55M in hexane) was gradually added maintaining an internal temperature below 0° C. during the addition.

The lithium pyrrolidide thus prepared was added to the cooled solution of the potassium carboxylate via cannula, maintaining an internal temperature below −30° C. throughout the addition. The clear yellow solution was aged between −35° to −30° C. for 2 hours. A solution of methyl bromide (2.36, 24.8 mmol) in tetrahydrofuran was added maintaining an internal temperature of −20° C. The white slurry was aged for 1 hour at this temperature. A solution of pyrrolidine (1.6 ml, 19.16 mmol) in tetrahydrofuran (15 ml) was cooled to −5° C. and n-butyllithium (12 ml, 18.6 mmol, 1.55M in hexane) was added maintaining the temperature below 0° C. This solution was gradually added to the reaction mixture maintaining an internal temperature below −30° C. The mixture was aged at −30° to −35° C. for 2 hours. A solution of methyl bromide (3.01 g, 31.7 mmol) in tetrahydrofuran was added maintaining an internal temperature of −20° C. The mixture was aged at that temperature for 1 hour.

The mixture was quenched into a vessel containing water (100 ml), the layers separated and the lower (aqueous) phase adjusted to pH 4.5 with 20% aqueous phosphoric acid. The acidified aqueous phase was extracted three times with 100 ml of cyclohexane. The combined cyclohexane extracts were washed twice with 50 ml of water, then dried over sodium sulfate (25 g). The mixture was filtered and slowly concentrated to a volume of 40 ml via distillation over 5 hours. After cooling to ambient temperature, the mixture was filtered to give crude product (4.15-4.25 g) of approximately 90-92% purity. The product was dissolved in methanol (22 ml/g of substrate) and water (6.2 ml/g) with stirring at 65° C. while additional water (6.2 ml/g) was added. The mixture was aged at ambient temperature overnight, filtered and dried under vacuum at 50° C. to yield pure product (85-92% recovery). Overall yield from trans-tetrahydro mevinolin is 67-75%.

Alternate Step B

The potassium salt of trans-tetrahydromevinolin (20 g, 49 mmole) is prepared in cyclohexane (400 ml), isopropanol (48 ml) and aqueous potassium hydroxide (10 ml, 4.91 Molar) as described above. The mixture is concentrated by distillation at atmospheric pressure. Additional cyclohexane (450 ml) is added. A total of 600 ml of distillate is collected. A K.F. of less than 70 μg H$_2$O/ml should be observed. The mixture is concentrated to a total volume of 52 ml.

Tetrahydrofuran (280 ml) and pyrrolidine (16 ml) is charged into the vessel and the solution cooled to less than −55° C. Butyl lithium (110 ml, 1.55M) is slowly added to the well stirred mixture, maintaining an internal temperature below −55° C. throughout the addition. The mixture is aged at −30° to −35° C. for 2.5 hours. Methyl bromide (10.0 g) is bubbled into the solution maintaining an internal temperature of −20° to −25° C. After an age of 15 minutes HPLC analysis is performed to confirm greater than 93% conversion. If less than 93% conversion is observed a second charge of methyl bromide (normally 0.25-0.75 g) is introduced. The mixture is aged at −20° to −25° C. for a total of one hour. Tetrahydrofuran (60 ml) and pyrrolidine (6.4 ml) are charged to the reaction mixture and cooled to less than −55° C. n-BuLi (48 ml, 1.55M) is slowly added as before maintaining an internal temperature below −55° C. during the addition. The mixture is aged for 2 hours at −30° to −35° C. Methyl bromide (12 g) is introduced as described above and the mixture aged for 1 hour at −20° to −25° C. The reaction mixture is quenched into 400 ml of H$_2$O and worked up and relactonized as described above. The crude yield after filtration of cyclohexane slurry and drying (40° C. in vacuo) 17.89 g, 86.9% pure. Overall yield is 75.2%.

EXAMPLE 2

6(R)-[2-[8(S)(2,2-dimethylbutyryloxy)-2(S),6(S)-dimethyl-1,2,3,4,4a,(S),5,6,7,8,8a(S)-decahydronaphthyl-1(S)]ethyl]-4(R)-hydroxy-3,4,5,6-tetrahydro-2H-pyran-2-one Step A: Preparation of 6(R)-[2-[8(S)(2,2-dimethylbutryloxy)-2(S),6(S)-dimethyl-1,2,6,7,8,8a(S)-hexahydronaphthyl-1(S)]ethyl]-4(R)-hydroxy-3,4,5,6-tetrahydro-2H-pyran-2-one Employing the procedure substantially as described in Example 1, Step B, or its alternate but substituting for the tetrahydro-mevinolin used as starting material therein, an equimolar amount of mevinolin, there was produced the title compound, (50-64% yield).

Step B: Preparation of 6(R)-[2-[8(S)(2,2-dimethylbutyryloxy)-2(S),6(S)-dimethyl-1,2,3,4,4a(S),5,6,7,8,8a(S)-decahydronaphthyl-1(S)]ethyl]-4(R)-hydroxy-3,4,5,6-tetrahydro-2H-pyran-2-one Employing the procedure substantially as described in Example 1, Step A, but substituting for the mevinolin used therein, an equimolar amount of the product from Step A of this Example 2, there was produced the title compound.

What is claimed is:

1. A process for the preparation of a compound of structural formula:

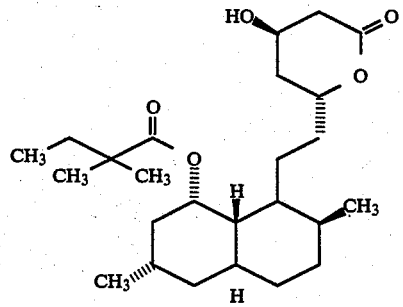

which comprises the steps in either order of
 (1) catalytic reduction of the two double bonds of the mevinolin molecule with a platinum on alumina catalyst in an organic solvent with agitation; and
 (2) C-methylation of the 2-methylbutryloxy side chain of the alkali metal salt of the mevinolin molecule with a methylating agent selected from methyl bromide, methyl chloride or methyl iodide and a strong base selected from alkali metal amide wherein the alkali metal is lithium, sodium or potassium and the amide is diethyl amide, pyrrolidide, dimethyl amide or diisopropyl amide and then relactonization with aqueous mineral acid selected from hydrochloric, hydrobromic, sulfuric or phosphoric acid.

2. The process of claim 1 wherein the two steps are in the order of reduction followed by C-alkylation.

3. The process of claim 1 wherein
 (1) the reduction step utilizes a 2-10% Pt/Al$_2$O$_3$ catalyst; the solvent is selected from ethyl acetate, isopropyl acetate, hexanes, and methylene chloride; the hydrogen pressure is atmospheric or higher; and the temperature is 15°-40° C.

(2) the C-methylation step is conducted with methyl iodide or methyl bromide in an ethereal solvent at −50° to −25° C. in the presence of an alkali metal amide wherein the alkali metal is sodium, potassium or lithium and the amide is diethylamide, dimethylamide, pyrrolidide or diisopropylamide.

4. The process of claim 3 wherein the two steps are in the order of reduction followed by alkylation.

5. The process of claim 3 wherein (1) the reduction step utilizes 5% $Pt/Al_2O_3$, ethyl acetate, and 40 psi of hydrogen, at 20°–25° C.; and
(2) the C-methylation step utilizes methyl iodide or methyl bromide, in tetrahydrofuran, at −35° to −30° C. in the presence of lithium diethylamide or lithium pyrrolidide.

6. The process of claim 5 wherein the two steps are in the order of reduction followed by alkylation.

* * * * *